United States Patent
Reddy et al.

(10) Patent No.: US 7,501,515 B2
(45) Date of Patent: Mar. 10, 2009

(54) POLYMORPHIC FORM OF 17-β-(N-TER. BUTYL CARBAMOYL)-4-AZA-5-α-ANDROST-1-EN-3-ONE

(75) Inventors: M. Satyanarayana Reddy, Hyderabad (IN); S. T. Rajan, Hyderabad (IN); M. V. N. Brahmeshwara Rao, Hyderabad (IN); K. Vyas, Hyderabad (IN); S. Vishnuvardhana Reddy, Hyderabad (IN); K. Shashi Rekha, Hyderabad (IN)

(73) Assignees: Dr. Reddy's Laboratories Limited, Hyderabad, Andhra Pradesh (IN); Dr. Reddy's Laboratories, Inc., Bridgewater, NJ (US)

( * ) Notice: Subject to any disclaimer, the term of this patent is extended or adjusted under 35 U.S.C. 154(b) by 971 days.

(21) Appl. No.: 10/801,069

(22) Filed: Mar. 15, 2004

(65) Prior Publication Data

US 2005/0059691 A1    Mar. 17, 2005

Related U.S. Application Data

(63) Continuation of application No. 10/363,719, filed as application No. PCT/US01/19546 on Jun. 19, 2001, now abandoned.

(30) Foreign Application Priority Data

Sep. 7, 2000    (IN)    ......................... 737/MAS/2000

(51) Int. Cl.
    C07D 221/18    (2006.01)
    C07D 221/04    (2006.01)
(52) U.S. Cl. .......................................... 546/77; 546/61
(58) Field of Classification Search ................... 546/77, 546/61
    See application file for complete search history.

(56) References Cited

U.S. PATENT DOCUMENTS 5,652,365 A    7/1997    McCauley et al. ............. 546/77

5,886,184 A    3/1999    Dolling et al. ................. 546/77

FOREIGN PATENT DOCUMENTS

| EP | 0298652 | 1/1989 |
|----|---------|--------|
| EP | 0367502 | 5/1990 |
| EP | 0428366 | 5/1991 |
| EP | 0473226 | 3/1992 |
| EP | 0599376 | 6/1994 |

OTHER PUBLICATIONS

Lorenc, Ijubinka et al: "Partial Synthesis of . . . Carboxamide"; J. Serb. Chem. Soc. (1993) 58(12), 991-5; XP001030462; p. 994, Paragraph 4.
Xia, Peng et al; "Synthesis of N-Substituted . . . Androstenes"; Heterocycles (1998), 47(2) 703-716, XP002179346; p. 712, Paragraph 2.
Bhattacharya A et al: "Acylimidazolides . . . of Proscar"; Synthetic . . . Inc., Basel, CH, vol. 30, No. 17, 1990, pp. 2683-2690, XP000944091, ISSN: 0039-7911, p. 2686, 11.
Bhattacharya, Apurba et al: "Silylation-Mediation . . . Adducts"; J.Am. Chem. Soc. (1998) 110(10), 3318-19, XP002179347; p. 3319, col. 1, Paragraph 1.

*Primary Examiner*—Charanjit S Aulakh
(74) *Attorney, Agent, or Firm*—Robert A. Franks; Lee C. Banks; Anjum Swaroop

(57) ABSTRACT

The present invention relates to a novel polymorphic form of 17-β-(N-ter.butyl carbamoyl)-4-aza-5-α-androst-1-en-3-one (Finasteride) of the Formula (I) and processes for preparing the form.

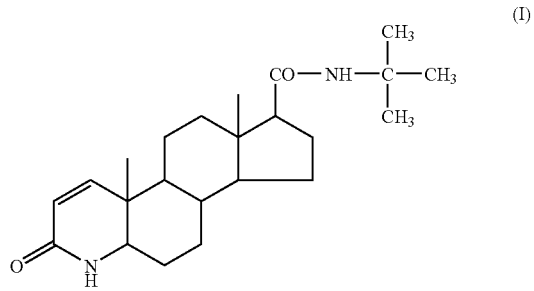

(I)

15 Claims, 3 Drawing Sheets

INFRARED SPECTRA of Form - III

POLYMORPHIC FORM OF 17-β-(N-TER. BUTYL CARBAMOYL)-4-AZA-5-α-ANDROST-1-EN-3-ONE

This application is a continuation of application Ser. No. 10/363,719 deposited on Mar. 7, 2003 now abandoned, which is International Application PCT/US01/19546 filed on Jun. 19, 2001, which designated the U.S., claims the benefit thereof and incorporates the same by reference.

FIELD OF INVENTION

The present invention relates to a novel polymorphic form of 17-β-(N-ter. butyl carbamoyl)-4-aza-5-α-androst-1-en-3-one (Finasteride) of the formula (I)

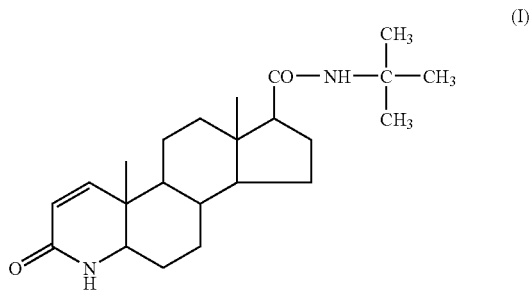

The present invention also relates to process for preparing the novel polymorphic form of 17-β-(N-ter. butyl carbamoyl)-4-aza-5-α-androst-1-en-3-one of the formula (I).

The polymorphic form of 17-β-(N-ter. butyl carbamoyl)-4-aza-5-α-androst-1-en-3-one (5-alpha reductase inhibitor) is useful in treating acne, female hirsutism and particularly benign prostatic hyperplasia.

BACKGROUND OF INVENTION

Polymorphism can be defined as the ability of the same chemical substance to exist in different crystalline structures. The different structures are are referred to as polymorphs, polymorphic modification or form.

It has been known that 17-β-N-ter. butyl carbamoyl)-4-aza-5-α-androst-1-en-3-one exists in two polymorphic forms i.e., Form-I and Form-II which are patented by Merck & Co. Inc. (U.S. Pat. Nos. 5,652,365 and 5,886,184)

The polymorphic form-I is characterized by a differential scanning calorimetry (DSC) curve, at heating rate of 20° C./min and in a closed cup, exhibiting a minor endotherm with a peak temperature of about 232° C.; an extrapolated onset temperature of about 223° C. with an associated heat of about 11 joules/gm and by a major melting endotherm with a peak temperature of about of 261° C.; an extrapolated onset temperature of about 258° C. with an associated heat of about 89 J/gm. The X-ray powder diffraction pattern is characterized by d-spacings of 6.44, 5.69, 5.36, 4.89, 4.55, 4.31, 3.85, 3.59 and 3.14. The FT-IR spectrum (in KBr) shows bands at 3431, 3237, 1692, 1666, 1602 and 688 cm−1.

The polymorphic form-II is characterized by a differential scanning calorimetry (DSC) curve, at heating rate of 20° C./min and in a closed cup, exhibiting a single melting endotherm with a peak temperature of about 261° C.; an extrapolated onset temperature of about 258° C., with an associated heat of about 89 J/g. The X-ray powder diffraction pattern is characterized by d-spacings of 14.09, 10.36, 7.92, 7.18, 6.40, 5.93, 5.66, 5.31, 4.68, 3.90, 3.60 and 3.25. The FT-IR spectrum (in KBr) shows bands at 3441, 3215, 1678, 1654, 1597, 1476 and 752 cm−1.

Two polymorphic forms and two pseudopolymorphic forms have been characterized using single crystal X-ray diffraction studies by Irena Wawrzycka et al and the results are published in the Journal of Molecular Structure, 474 (1999) 157-166.

The two polymorphic forms referred as 1 and 2 are same as the Form-I and Form-II mentioned above.

The pseudopolymorphic form 1a crystallizes in Monoclinic space group $P2_1$ with cell dimensions a=12.120(1), b=8.1652(7), c=13.577(1)A°, β=111.530° containing two molecules in unit cell. The lattice contains one molecule of acetic acid. It decomposes losing acetic acid and recrystallizes in the range 170-174° C. having melting point 255-257° C.

The pseudopolymorphic form 1b crystallizes in orthorhombic space group $P2_12_12_1$ having cell dimensions a=8.173 (3), b=18.364 (6), c=35.65 (2) containing four molecules in unit cell. The lattice contains one molecule of ethyl acetate for two molecules of Finasteride. The melting point of form 1b is reported as 252-255° C.

While doing process development to optimize the yield and quality of 17-β-(N-ter. butyl carbamoyl)-4-aza-5-α-androst-1-en-3-one, different crystallization and isolation methods were used with different combinations of organic solvents and by varying the various parameters like temperature and volume etc.

All samples which were isolated in different methods were submitted for regular analysis and subjected to polymorphic characterizations studies. From this we found that 17-β-(N-ter. butyl carbamoyl)-4-aza-5-α-androst-1-en-3-one exists in additional polymorphic/pseudopolymorphic forms namely Form-III, Form-IV, and Form-V which are different from Form-I and Form-II disclosed in the prior art.

The XRD data and thermal characteristics of the pseudopolymorphic forms Form-IV and Form-V reasonably match with those of the pseudopolymorphs 1b and 1a mentioned above respectively.

SUMMARY OF INVENTION

Figure 1:
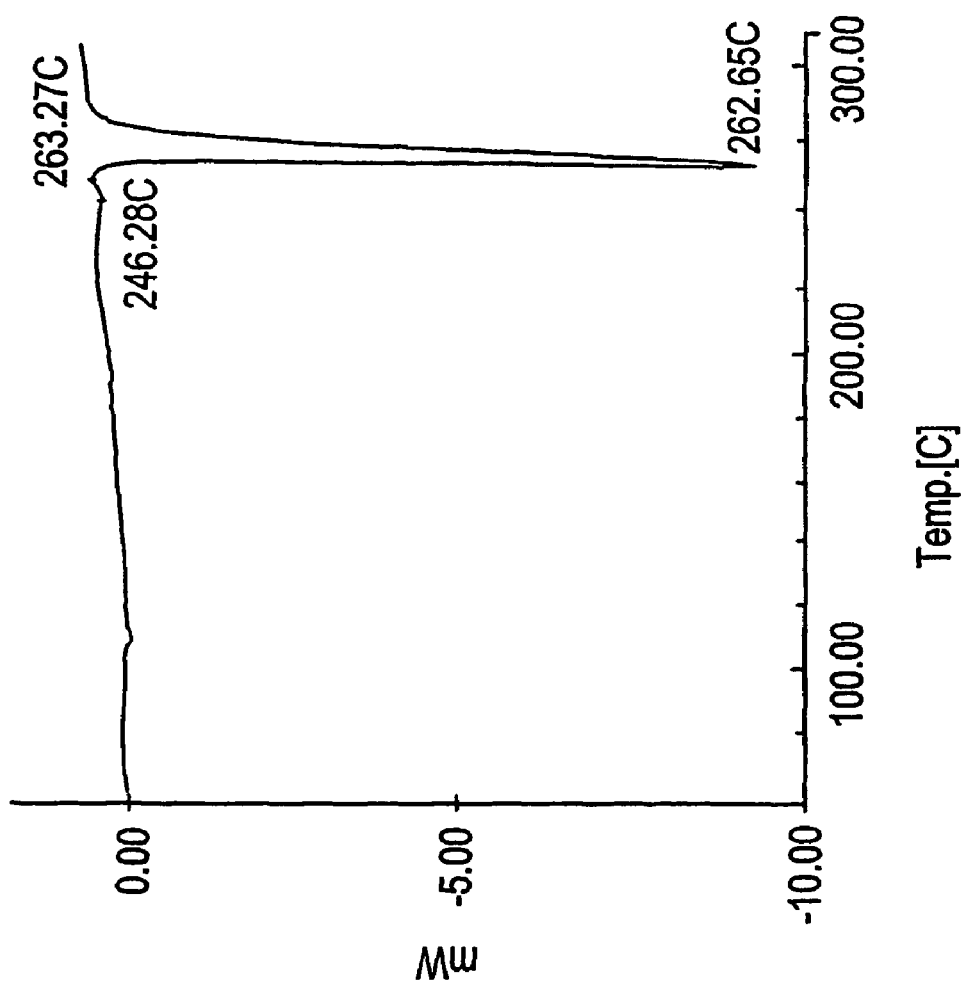
FIG. 1: Differential scanning calorimetry of Form-III.

Accordingly, the present invention provides a novel polymorphic form, Form-III of 17-β-(N-ter. butyl carbamoyl)-4-aza-5-α-androst-1-en-3-one which is characterized by the following data:

DSC: exhibits a melting endotherm with a peak temperature of about 262° C. and preceded by another minor endotherm at about 245° C. and an exotherm at about 253° C. (FIG. 1)

Figure 2:
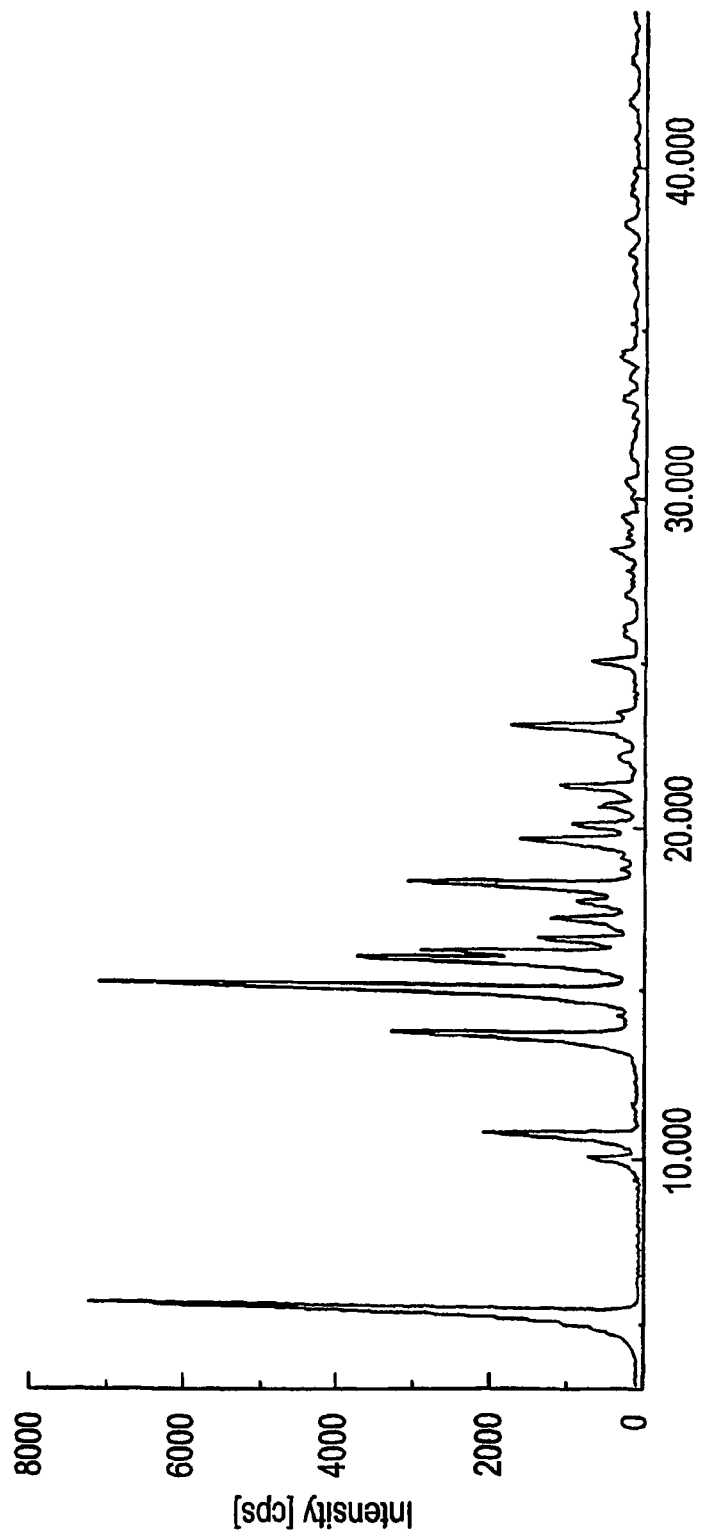
FIG. 2: X-Ray powder diffractogram of Form-III.

XRD (2θ): 5.32, 10.70, 13.64, 14.96, 15.86, 16.12, 16.56, 17.20, 18.22, 19.60, and 23.04. (FIG. 2)

Figure 3:
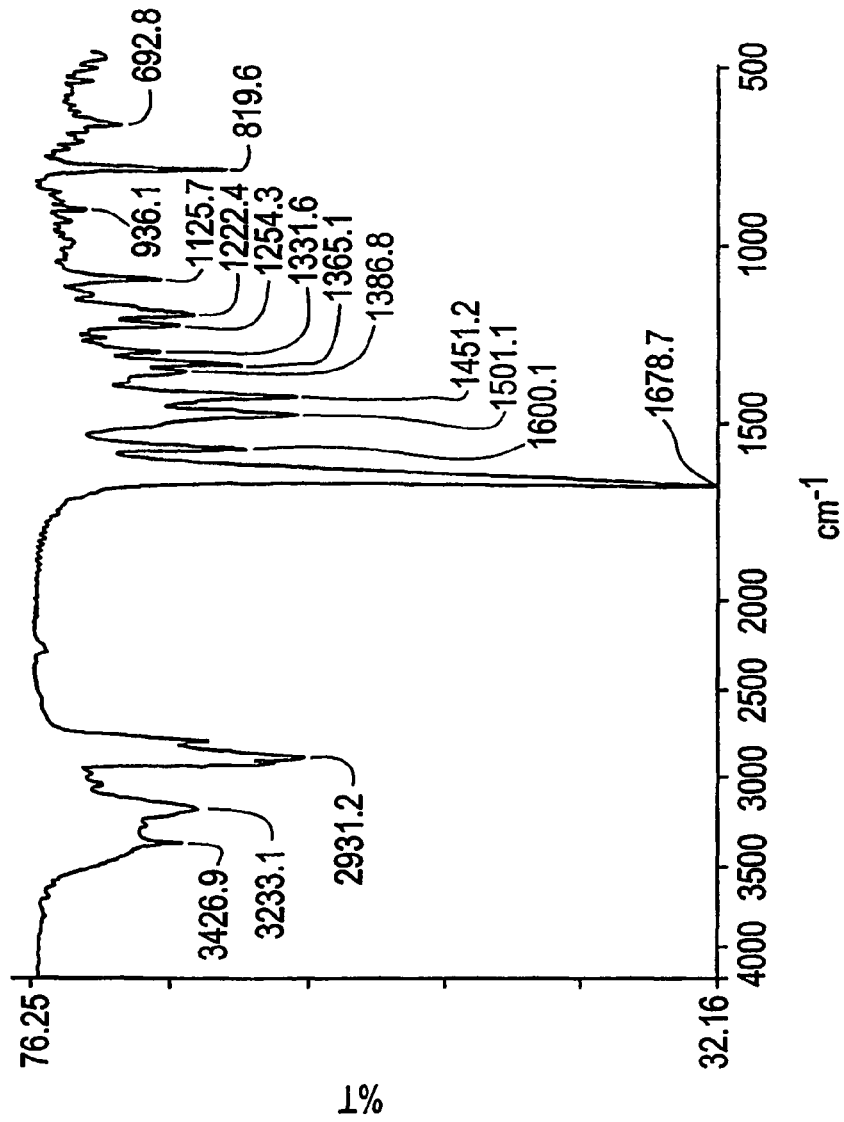
FIG. 3: Infrared Spectra of Form-III.

FT-IR (In KBr): 3427, 3233, 2931, 1679, 1600, 1501, 1451 and 820 cm$^{-1}$. (FIG. 3)

According to another embodiment of the present invention, there is provided processes for preparing Form-III, Form-IV and Form-V of 17-β-(N-ter. butyl carbamoyl)-4-aza-5-α-androst-1-en-3-one of formula (I).

DETAILED DESCRIPTION OF THE INVENTION

The present invention provides a novel polymorphic form, Form-III of 17-β-(N-ter. butyl carbamoyl)-4-aza-5-α-androst-1-en-3-one which is characterized by the following data:

DSC: exhibits a melting endotherm with a peak temperature of about 262° C. and preceded by another minor endotherm at about 245° C. and an exotherm at about 253° C. (FIG. 1)

XRD (2θ): 5.32, 10.70, 13.64, 14.96, 15.86, 16.12, 16.56, 17.20, 18.22, 19.60, and 23.04. (FIG. 2)

FT-IR (In KBr): 3427, 3233, 2931, 1679, 1600, 1501, 1451 and 820 cm$^{-1}$. (FIG. 3)

According to another embodiment of the present invention, there is provided a process for preparing Form-III of 17-β-(N-ter. butyl carbamoyl)-4-aza-5-α-androst-1-en-3-one of formula (I), which comprises:

(i) dissolving the crude 17-β-(N-ter. butyl carbamoyl)-4-aza-5-α-androst-1-en-3-one in water immiscible organic, solvents, such as halogenated solvent or aromatic hydrocarbon solvent or organic solvents selected from alkyl acetates;

(ii) saturating the solution with less polar organic solvent, selected from aliphatic hydrocarbon either straight chain or branched, preferably hexane or heptane; or petroleum ether; and.

(iii) concentrating the solution and isolating the Form-III of 17-β-(N-ter. butyl carbamoyl)-4-aza-5-α-androst-1-en-3-one of formula (I) by conventional methods.

According to another embodiment of the present invention, there is provided an alternate process for preparing the Form-III of 17-β-(N-ter. butyl carbamoyl)-4-aza-5-α-androst-1-en-3-one of formula (I), which comprises, (i) dissolving any of the Form-I, Form-II, Form-IV and Form-V of 17-β-(N-ter. butyl carbamoyl)-4-aza-5-α-androst-1-en-3-one of formula (I) in water immiscible organic solvents such as halogenated solvent or aromatic hydrocarbon solvent or organic solvents selected from alkyl acetates;

(ii) distilling off 60-70% of the solvent;

(iii) saturating the remaining solution with less polar organic solvents selected from aliphatic hydrocarbon either straight chain or branched, preferably hexane or heptane, or petroleum ether, and (iv) concentrating the resultant solution and isolating the Form-III of 17-β-(N-ter. butyl carbamoyl)-4-aza-5-α-androst-1-en-3-one of formula (I) by conventional methods.

Process used for the preparation of Form-IV and Form-V of 17-β-(N-ter. butyl carbamoyl)-4-aza-5-α-androst-1-en-3-one of formula (I), are herein incorporated as reference.

Form-IV of 17-β-(N-ter. butyl carbamoyl)-4-aza-5-α-androst-1-en-3-one can be prepared by a process, which comprises:

(i) preparing a slurry of 17-β-(N-ter. butyl carbamoyl) aza-5-α-androst-1-en-3-one in ethyl acetate, tetrahydrofuran and water mixture such that the ratio of ethyl acetate:tetrahydrofuran:water is 1:1:~0.1 and the ratio of this solvent mixture used is 1-3 volume/weight of 17-β-(N-ter. butyl carbamoyl)-4-aza-5-α-androst-1-en-3-one;

(ii) heating the resultant slurry to a temperature of 50 to 60° C., (iii) cooling the slurry to −5 to 5° C.; and (iv) recovering the resultant solid by filtration and washing with chilled mixture of ethyl acetate and tetrahydrofuran and with petroleum ether to yield Form-IV of 17-β-(N-ter. butyl carbamoyl)-4-aza-5-α-androst-1-en-3-one of formula (I).

Form-V of 17-β-(N-ter. butyl carbamoyl)-4-aza-5-α-androst-1-en-3-one of formula (I), can be prepared by a process which comprises:

(i) dissolving 17-β-(N-ter. butyl carbamoyl)-4-aza-5-α-androst-1-en-3-one of formula (I) in aqueous acetic acid, that is acetic acid:water in a ratio of 4:6, such that the amount of aqueous acetic acid is 5-15 volume/weight of 17-β-(N-ter. butyl carbamoyl)-4-aza-5-α-androst-1-en-3-one;

(ii) heating the resultant mixture to 70-80° C.;

(iii) cooling to 10-20° C.; and (iv) filtering the resulting material and isolating the Form-V of 17-β-(N-ter. butyl carbamoyl)-4-aza-5-α-androst-1-en-3-one of formula (I) by conventional methods.

The water immiscible organic solvent used in the process of preparing Form-III of 17-β-(N-ter. butyl carbamoyl)-4-aza-5-α-androst-1-en-3-one include any solvents such as halogenated solvent selected from dichloromethane or chloroform or aromatic hydrocarbon solvent preferably toluene or organic solvents selected from alkyl acetates preferably ethyl acetate.

In the process for the preparation of Form-III polymorph, 17-β-(N-ter. butyl carbamoyl)-4-aza-5-α-androst-1-en-3-one is dissolved in halogenated solvent such that the amount of halogenated solvent is 1-10 volume/weight of 17-β-(N-ter. butyl carbamoyl)-4-aza-5-α-androst-1-en-3-one.

In case where the selected is aromatic hydrocarbon solvent preferably toluene, the amount of aromatic hydrocarbon solvent is 25-50 volume/weight of 17-β-(N-ter. butyl carbamoyl)-4-aza-5-α-androst-1-en-3-one.

In case where the selected solvent is alkyl acetates preferably ethyl acetate, the alkyl acetate solvent is 10-20 volume/weight of 17-β-(N-ter. butyl carbamoyl)-4-aza-5-α-androst-1-en-3-one.

The solvent selected are those in which 17-β-(N-ter. butyl carbamoyl)-4-aza-5-α-androst-1-en-3-one can be dissolved at room temperature (25-35° C.) as in the case of halogenated solvents or else at elevated temperatures preferably at 40-50° C., as in case of aromatic hydrocarbon solvent or organic solvents selected from alkyl acetates, until dissolution is achieved.

Less polar organic solvents as used herein are meant to include solvents selected from C5-C10 aliphatic hydrocarbons either straight chain or branched, preferably hexane or heptane or petroleum ether, which precipitate 17-β-(N-ter. butyl carbamoyl)-4-aza-5-α-androst-1-en-3-one from the solution. The step of saturating with a less polar organic solvent is carried out at a temperature in the range of 25-60° C.

The present invention is described in the examples below, which can be provided by way of illustration only and does not limit the scope of the invention.

EXAMPLE 1

Preparation of Crude Finasteride

17β-(N-ter. Butyl carbamoyl)-4-aza-5-α-androstane-3-one (1 gm) is reacted with 2,3 dichloro 5,6 dicyano benzoquinone (0.7 gm and Bis-(trimethylsilyl) Trifluoroacetamide (2.5 gm) in toluene (25 ml) medium at 80-110° C. After completion of reaction, toluene layer was washed with 5-10% aqueous sodium sulphite solution (80 ml), and then with water (200 ml). The toluene is stripped under vacuum to yield residual solid that is crude Finasteride.

EXAMPLE 2

Conversion of Crude Finasteride to Form III

Crude Finasteride was dissolved in methylene chloride (3 ml) at 25-35° C. This methylene chloride was saturated with petroleum ether (20 ml) at 25-30° C. under stirring. The separated solid, after removal of methylene chloride and petroleum ether under reduced pressure at 50-60° C. is isolated with petroleum ether (2 ml) at 10-15° C. This solid was dried at ambient temperature. (yield: 0.8 gm)

EXAMPLE 3

Conversion of Finasteride Form I to Form III

Form-I of 17-β-N-ter. butyl carbamoyl)-4-aza-5-α-androst-1-en-3-one (1 gm) was dissolved in methylene chloride (3 ml) and 60-70% of the methylene chloride was distilled off at 40-45° C. The resultant solution was saturated with petroleum ether (10 ml) at 40-60° C. under stirring. The solution was concentrated at 60-65° C. at atmospheric pressure and then the resultant residual solid was kept under vacuum at 60-65° C. for about 30 minutes.

The solid so obtained was isolated and dried in oven at 70-90° C. for 8-12 h, to yield Form-III of 17-β-(N-ter. butyl carbamoyl)-4-aza-5-α-androst-1-en-3-one (yield: 0.9 gm)

EXAMPLE 4

Conversion of Finasteride Form I to Form III

Form-I of 17-β-(N-ter. butyl carbamoyl)-4-aza-5-α-androst-1-en-3-one (1 gm) was dissolved in chloroform (3 ml) and 60-70% of the chloroform was distilled off at 60-70° C. The resultant solution was saturated with petroleum ether (10 ml) at 40-60° C. under stirring. The solution was concentrated at 60-65° C. at atmospheric pressure and the resultant residual solid was kept under vacuum at 60-65° C. for 30 min. The solid so obtained was isolated and dried in oven at 70-90° C. for 8-12 h, to yield Form-III of 17-β-(N-ter. butyl carbamoyl)-4-aza-5-α-androst-1-en-3-one (yield: 0.9 gm)

EXAMPLE 5

Conversion of Finasteride Form II to Form III

Form-II of 17-β-(N-ter. butyl carbamoyl)-4-aza-5-α-androst-1-en-3-one (1 gm) was dissolved in methylene chloride (3 ml) and 60-70% of the methylene chloride was distilled off at 40-45° C. The resultant solution was saturated with pet ether (10 ml) at 40-60° C. under stirring. The solution was concentrated at 60-65° C. at atmospheric pressure and then the resultant residual solid was kept under vacuum at 60-65° C. for 30 min. The solid so obtained was isolated and dried in oven at 70-90° C. for 8-12 h, to yield Form-III of 17-β-(N-ter. butyl carbamoyl)-4-aza-5-α-androst-1-en-3-one. (yield: 0.9 gm)

EXAMPLE 6

Conversion of Finasteride Form II to Form III

Form-II of 17-β-(N-ter. butyl carbamoyl)-4-aza-5-α-androst-1-en-3-one (1 gm) was dissolved in chloroform (3 ml) and 60-70% of the chloroform was distilled off at 60-70° C. The resultant solution was saturated with petroleum ether (10 ml) at 40-60° C. under stirring. The solution was concentrated at 60-65° C. atmospheric pressure and then the resultant residual solid was kept under vacuum at 60-65° C. for 30 min. The solid so obtained was isolated and dried in oven at 70-90° C. for 8-12 h, to yield Form-III of 17-β-N-ter. butyl carbamoyl)-4-aza-5-α-androst-1-en-3-one. (yield: 0.9 gm)

EXAMPLE 7

Conversion of Finasteride Form IV to Form III

Form IV of 17-β-(N-ter. butyl carbamoyl)-4-aza-5-α-androst-1-en-3-one (1.0 gm) was dissolved in methylene chloride (3 ml) and 60-70% of the methylene chloride was distilled off at 40-45° C. The resultant solution was saturated with petroleum ether (10 ml) at 40-60° C. under stirring. The solution was concentrated at 60-65° C. at atmospheric pressure and then the resultant residual solid was kept under vacuum at 60-65° C. for 30 min. The solid so obtained was isolated and dried in oven at 70-90° C. for 8-12 h, to yield Form-III of 17-β-(N-ter. butyl carbamoyl)-4-aza-5-α-androst-1-en-3-one. (yield: 0.8 gm)

EXAMPLE 8

Conversion of Finastride Form IV to Form III

Form-IV of 17-β-(N-ter. butyl carbamoyl)-4-aza-5-α-androst-1-en-3-one (1 gm) was dissolved in chloroform (3 ml) and 60-70% of the chloroform was distilled off at 60-70° C. The resultant solution was saturated with petroleum ether (10 ml) at 40-60° C. under stirring. The solution was concentrated at 60-65° C. at atmospheric pressure and the resultant residual solid was kept under vacuum at 60-65° C. for 30 min. The solid so obtained was isolated and dried in oven at 70-90° C. for 8-12 hrs, to yield Form-III of 17-β-N-ter. butyl carbamoyl)-4-aza-5-α-androst-1-en-3-one. (yield: 0.8 gm)

EXAMPLE 9

Conversion of Finastride Form V to Form III

Form-V of 17-β-(N-ter. butyl carbamoyl)-4-aza-5-α-androst-1-en-3-one (1 gm) was dissolved in methylene chloride (3 ml) and 60-70% of the methylene chloride was distilled off at 40-45° C. The resultant solution was saturated with petroleum ether (10 ml) at 40-60° C. under stirring. The solution was concentrated at 60-65° C. at atmospheric pressure and the resultant residual solid was kept under vacuum at 60-65° C. for 30 min. The solid so obtained was isolated and dried in oven at 70-90° C. for 8-12 h, to yield Form-III of 17-β-(N-ter. butyl carbamoyl)-4-aza-5-α-androst-1-en-3-one. (yield 0.7 gm)

EXAMPLE 10

Conversion of Finastride Form V to Form III

Form-V of 17-β-(N-ter. butyl carbamoyl)-4-aza-5-α-androst-1-en-3-one (1 gm) was dissolved in chloroform (3 ml) and 60-70% of the chloroform was distilled off at 60-70° C. The resultant solution was saturated with pet. ether (10 ml) at 40-60° C. under stirring. The solution was concentrated at 60-65° C. atmospheric pressure and then the resultant residual solid was kept under vacuum at 60-65° C. for 30 min.

The solid so obtained was isolated and dried in oven at 70-90° C. for 8-12 h, to yield Form-III of 17-β-(N-ter. butyl carbamoyl)-4-aza-5-α-androst-1-en-3-one. (yield: 0.7 gm)

EXAMPLE 11

Preparation of Finasteride Form IV

Form-IV can be prepared by heating 17-β-(N-ter. butyl carbamoyl)-4-aza- 5-α-androst-1-en-3-one (1 gm) in ethyl acetate, tetrahydrofuran and water mixture (1.5 ml+1.5 ml+0.1 ml) at 50-60° C. for 25-30 min and cooling at −5° C. to 5° C. for 30-45 min. The resulting solid was separated by filtration and washed with chilled mixture of ethyl acetate and tetrahydrofuran (0.5 ml+0.5 ml) and finally with petroleum ether (1 ml) and dried. (yield: 1.1 gm)

Any of Forms I, II, III or V can be used to prepared Form IV.

EXAMPLE 12

Preparation of Finasteride Form V

Form-V can be prepared by heating 17-β-(N-ter. butyl carbamoyl)-4-aza- 5-α-androst-1-en-3-one (1 gm) in aqueous acetic acid (7 ml) (i.e., acetic acid:water 4:6) at 70-80° C. for about 25-30 min. After cooling the mixture at 10-20° C. for 8-9 hours, the resultant solid was filtered and washed with water and suck dried. (yield: 0.8 gm)

Any of Forms I, II, III or IV can be used to prepare Form V.

The invention claimed is:

1. A polymorphic Form-III of 17-β-(N-ter. butyl carbamoyl)-4-aza-5-α-androst-1-en-3-one having the formula,

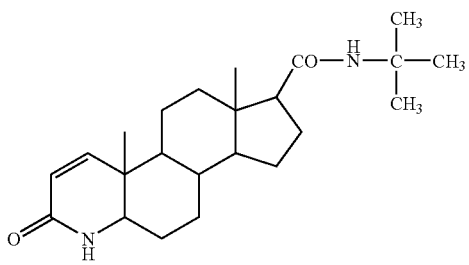

which is characterized by the following data:
DSC: exhibits a melting endotherm with a peak temperature of about 262° C. and preceded by another minor endotherm at about 245° C. and an exotherm at about 253° C.;
XRD (2θ): 5.32, 10.70, 13.64, 14.96, 15.86, 16.12, 16.56, 17.20, 18.22, 19.60, and 23.04;
FT-IR (In KBr): 3427, 3233, 2931, 1679, 1600, 1501,1451 and 820 cm$^{-1}$.

2. A process for preparing Form-III of 17-β-(N-ter. butyl carbamoyl-4-aza-5-α-androst-1-en-3-one, which comprises:
   (i) dissolving crude 17-β-(N-ter. butyl carbamoyl)-4-aza-5-α-androst-1-en-3-one in a water immiscible organic solvent,
   (ii) saturating the solution with an aliphatic hydrocarbon either straight chain or branched,
   (iii) concentrating the solution and isolating the Form III of 17-β-(N-ter. butyl carbamoyl)-4-aza-5-α-androst-1-en-3-one.

3. The process as claimed in claim 2, wherein the water immiscible organic solvent is selected from a halogenated solvent, an aromatic hydrocarbon solvent, or an alkyl acetate.

4. The process as claimed in claim 3, wherein the halogenated solvent is selected from dichloromethane or chloroform.

5. The process as claimed in claim 3, wherein the aromatic hydrocarbon solvent is toluene.

6. The process as claimed in claim 3, wherein the alkyl acetate is ethyl acetate.

7. A process for preparing the Form-III of 17-β-(N-ter. butyl carbamoyl)-4-aza-5-α-androst-1-en-3-one, which comprises,
   (i) dissolving any of the Form-I, Form-II, Form-IV and Form-V of 17-β-(N-ter. butyl carbamoyl)-4-aza-5-α-androst-1-en-3-one in a water immiscible organic solvent,
   (ii) distilling off 60-70% of the solvent,
   (iii) saturating the remaining solution with an aliphatic hydrocarbon either straight chain or branched, and
   (iv) concentrating the resultant solution and isolating the Form-III of 17-β-(N-ter. butyl carbamoyl)-4-aza-5-α-androst-1-en-3-one.

8. The process as claimed in claim 7, wherein the water immiscible organic solvent is selected from a halogenated solvent, an aromatic hydrocarbon solvent, or an alkyl acetate.

9. The process as claimed in claim 8, wherein the halogenated solvent is selected from dichloromethane or chloroform.

10. The process as claimed in claim 8, wherein the aromatic hydrocarbon solvent is toluene.

11. The process as claimed in claim 8, wherein the alkyl acetate is ethyl acetate.

12. Polymorphic Form-III of finasteride, having a differential scanning calorimetry curve substantially in accordance with the curve of FIG. 1.

13. Polymorphic Form-III of finasteride, having an X-ray powder diffraction pattern substantially in accordance with the pattern of FIG. 2.

14. Polymorphic Form-III of finasteride, having an infrared spectrum substantially in accordance with the spectrum of FIG. 3.

15. Polymorphic Form-III of finasteride, having a differential scanning calorimetry curve having a melting endotherm with a peak temperature of about 262° C., a minor endotherm at about 245° C., and an exotherm at about 253° C.

* * * * *